US011938048B2

(12) United States Patent
Su

(10) Patent No.: US 11,938,048 B2
(45) Date of Patent: Mar. 26, 2024

(54) FOOD REFLUX REDUCING TWO-PIECE NASOGASTRIC TUBE

(71) Applicant: Chien-Chung Su, Taichung (TW)

(72) Inventor: Chien-Chung Su, Taichung (TW)

(*) Notice: Subject to any disclaimer, the term of this patent is extended or adjusted under 35 U.S.C. 154(b) by 0 days.

(21) Appl. No.: 17/825,822

(22) Filed: May 26, 2022

(65) Prior Publication Data

US 2022/0378595 A1 Dec. 1, 2022

(30) Foreign Application Priority Data

May 27, 2021 (TW) ................. 110119282

(51) Int. Cl.
*A61F 5/00* (2006.01)
*F16L 37/088* (2006.01)
*F16L 37/098* (2006.01)

(52) U.S. Cl.
CPC ........ *A61F 5/0036* (2013.01); *F16L 37/0885* (2019.08); *F16L 37/0987* (2013.01); *F16L 2201/10* (2013.01)

(58) Field of Classification Search
CPC ............. A61M 39/1011; A61M 39/26; A61M 39/045; A61M 2039/1027; A61M 39/10; A61M 2039/1033; A61M 2039/267; A61M 39/04; A61M 2039/1072; A61M 2039/064; A61M 39/14; A61M 2025/024; A61M 16/0666; A61M 16/0672; A61M 16/0677; A61M 16/0683; A61M 16/0688; A61M 25/02; A61M 2039/1077; A61M 2025/0226; A61M 2025/028; A61M 16/0497; A61M 2025/0266; F16L 37/098; F16L 37/0982; F16L 37/0985;
(Continued)

(56) References Cited

U.S. PATENT DOCUMENTS 4,610,665 A * 9/1986 Matsumoto ....... A61M 39/0606
604/167.04
4,932,943 A * 6/1990 Nowak ................. A61M 25/02
604/178
(Continued)

FOREIGN PATENT DOCUMENTS

CN 2461587 Y 11/2001
CN 205494632 U 8/2016
(Continued)

*Primary Examiner* — Adam Marcetich
(74) *Attorney, Agent, or Firm* — Muncy, Geissler, Olds & Lowe, P.C.

(57) ABSTRACT

A food reflux reducing two-piece nasogastric tube includes a first tube body and a second tube body. The first tube body has a first connector on one end, and a protrusion edge on an outer side of the first connector in adjacent to the first positioning portion. The first connector has a through hole having a seal portion in adjacent to the first positioning portion. The seal portion has a cross break. A convex portion is on an inner edge of the through hole between the seal portion and the first positioning portion. The second tube body has one end provided with a second connector and an insertion combination tube extending therefrom. Two elastic arms extend from an outer side of the second connector and comprise a hook portion respectively. Thus, the second tube body is efficiently connected with and removed from the first tube body.

4 Claims, 8 Drawing Sheets

(58) Field of Classification Search
CPC .............. F16L 37/0987; Y10S 604/905; Y10T 403/32631; Y10T 403/32311; Y10T 403/32032; Y10T 403/32803; Y10T 403/32196; Y10T 403/32786; Y10T 403/32704; Y10T 74/18336; Y10T 403/32565; Y10T 403/32681; Y10T 29/49853; A61B 1/0014; A61B 2017/2926; A61B 2017/2927; A61B 2017/2929; A61B 2017/293; F16B 2/22; F16B 7/0433; F16M 11/14

See application file for complete search history.

(56) References Cited

U.S. PATENT DOCUMENTS

| | | | | |
|---|---|---|---|---|
| 5,334,179 | A * | 8/1994 | Poli | A61J 1/2089 604/411 |
| 5,476,091 | A * | 12/1995 | Johnson | A61M 29/00 602/56 |
| 5,603,706 | A * | 2/1997 | Wyatt | A61M 39/1011 285/361 |
| 5,752,511 | A * | 5/1998 | Simmons | A61M 16/0497 128/207.18 |
| 5,797,897 | A * | 8/1998 | Jepson | A61J 1/2089 604/533 |
| 5,810,792 | A * | 9/1998 | Fangrow, Jr. | A61M 39/045 604/533 |
| 5,820,614 | A * | 10/1998 | Erskine | F16L 55/1007 604/905 |
| 6,423,053 | B1 * | 7/2002 | Lee | A61M 39/1011 604/905 |
| 6,629,707 | B1 * | 10/2003 | Yamaguchi | F16L 37/0985 285/87 |
| 6,726,672 | B1 * | 4/2004 | Hanly | A61J 1/10 604/905 |
| 8,795,256 | B1 * | 8/2014 | Smith | A61M 39/26 604/249 |
| 2003/0050604 | A1 * | 3/2003 | Lui | A61M 39/0606 604/164.05 |
| 2005/0082828 | A1 * | 4/2005 | Wicks | F16L 37/38 285/320 |
| 2005/0192537 | A1 * | 9/2005 | Osborne | A61M 39/0606 604/167.01 |
| 2005/0256461 | A1 * | 11/2005 | DiFiore | A61M 39/26 604/537 |
| 2010/0030164 | A1 * | 2/2010 | Kimball | A61M 39/02 604/256 |
| 2010/0121281 | A1 * | 5/2010 | Luhrs | A61M 25/02 604/174 |
| 2010/0331787 | A1 * | 12/2010 | Fournie | A61M 39/1011 604/207 |
| 2013/0317483 | A1 * | 11/2013 | Reichart | A61M 39/1011 604/541 |
| 2014/0217718 | A1 * | 8/2014 | O'Donnell | G09F 3/14 493/324 |
| 2014/0358095 | A1 * | 12/2014 | Christensen | B65D 21/086 604/319 |
| 2014/0378907 | A1 | 12/2014 | Liu | |
| 2019/0001112 | A1 * | 1/2019 | Takeuchi | A61M 39/26 |
| 2022/0008708 | A1 * | 1/2022 | Takeuchi | A61M 39/10 |

FOREIGN PATENT DOCUMENTS

| | | |
|---|---|---|
| CN | 212235330 U | 12/2020 |
| TW | I438014 B | 5/2014 |
| TW | 202027814 A | 8/2020 |
| WO | WO-2008/146181 A1 | 12/2008 |

\* cited by examiner

FOOD REFLUX REDUCING TWO-PIECE NASOGASTRIC TUBE

BACKGROUND OF THE INVENTION

1. Field of the Invention

The present invention relates to nasogastric tubes, and more particularly, to a food reflux reducing two-piece nasogastric tube.

2. Description of the Related Art

With the development of technology and the progress of medicine, the survival rate of patient has been improved. However, when the patient is unable to eat by himself/herself due to injury, illness or elder age, the patient needs to be provided with irrigation feeding through a nasogastric tube feeder by medical staff. In other words, through an intubation manner, the food has to be processed into a liquid state and guided into the stomach through the nasal cavity for supplying the patient with necessary calories and nutrition.

However, the installation of the nasogastric tube always makes the patient quite uncomfortable. Also, after the intubation of a normal patient, the exposed parts of the nasogastric tube are directly adhered to the face of the patient. Such method is not only unstable, but also causing discomfort of the patient. Furthermore, the excessive nasogastric tube is exposed, significantly affecting the aesthetic appearance of the patient. Moreover, even if the exposed parts of the nasogastric tube are adhered on the face, it is almost impossible to prevent accidental pulling of the tube.

Therefore, a type of two-piece nasogastric tube is developed, comprising a first tube body and a second tube body connected thereto. The first tube body passes from the nasal cavity through the esophagus into the stomach of the patient, and the second tube body is exposed outside the nasal cavity, wherein the second tube body can be disassembled according to practical demand, so as to improve the issues above. Also, to prevent the first tube body from environmental pollution, and to prevent the reflux of food residue in the first tube body, when the second tube body is detached from the first tube body, a cover is applied to cover the opening of the first tube body.

SUMMARY OF THE INVENTION

In view of the above-mentioned shortcomings of the conventional two-piece nasogastric tube, the inventor has invented the present invention based on relative idea of creation through various discussions and sample trials after multidimensional revisions and improvements.

An embodiment of the present invention provides a food reflux reducing two-piece nasogastric tube, comprising: a first tube body having a first connector on one end and an insertion portion on another end, a first positioning portion disposed on one end of the first connector away from the first tube body, a protrusion edge being disposed on an outer side of the first connector in adjacent to the first positioning portion, the first connector comprising a through hole formed in an axial direction and connected with the first tube body, the through hole comprising an elastic seal portion disposed in adjacent to the first positioning portion, the seal portion being provided with a cross break which is normally in a sealing status, a convex portion disposed on an inner edge of the through hole between the seal portion and the first positioning portion; and a second tube body having an irrigation portion disposed on one end and a second connector disposed on another end, a second positioning portion disposed on one end of the second connector away from the second tube body, an insertion combination tube extending from the second positioning portion, the insertion combination tube being connected with the second tube body, two elastic arms extending from an outer side of the second connector toward the insertion combination tube, with a hook portion disposed on a distal end of each of the two elastic arms; wherein, when in use, the second connector is inserted into the through hole of the first connector through the insertion combination tube, such that the insertion combination tube expands the cross break, an outer periphery of the insertion combination tube tightly contacts and abuts against the convex portion, the second positioning portion abuts against the first positioning portion, and the hook portion of the two elastic arms hooks the protrusion edge, whereby the second connector is connected with the first connector, and the second tube body is connected with the first tube body.

Regarding the main objective of the food reflux reducing two-piece nasogastric tube of the present invention, when the second tube body is disassembled from the first tube body, the cross break of the first connector automatically closes, thereby significantly increasing the convenience of usage, lowering the discomfort of patients, and reducing the food reflux. Also, the conditions of the cover falling or the user forgetting to put on the cover are avoided.

DETAILED DESCRIPTION OF THE INVENTION

The aforementioned and further advantages and features of the present invention will be understood by reference to the description of the preferred embodiment in conjunction with the accompanying drawings where the components are illustrated based on a proportion for explanation but not subject to the actual component proportion.

Figure 1:
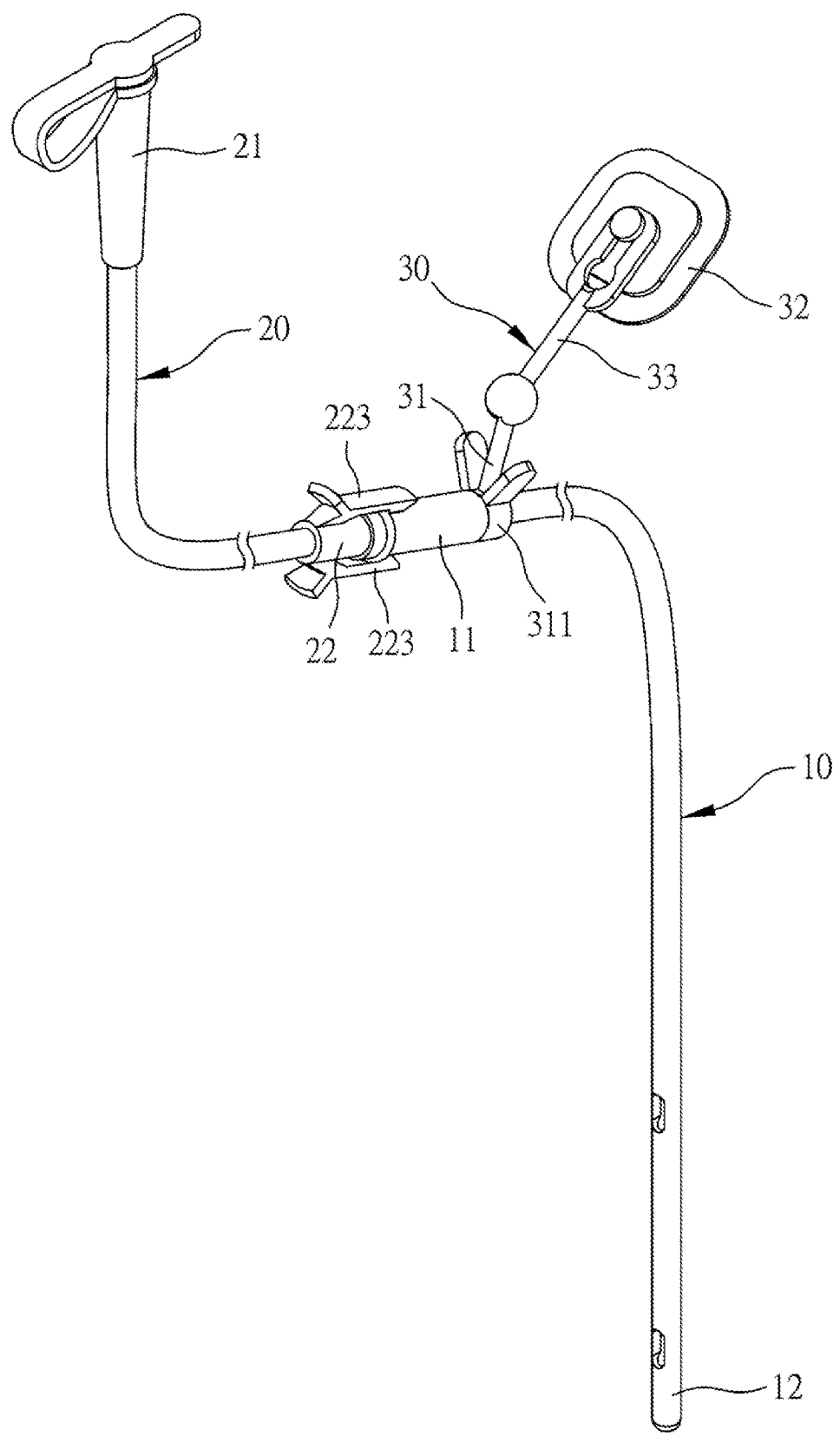
FIG. 1 is a perspective view of the present invention.
Figure 2:
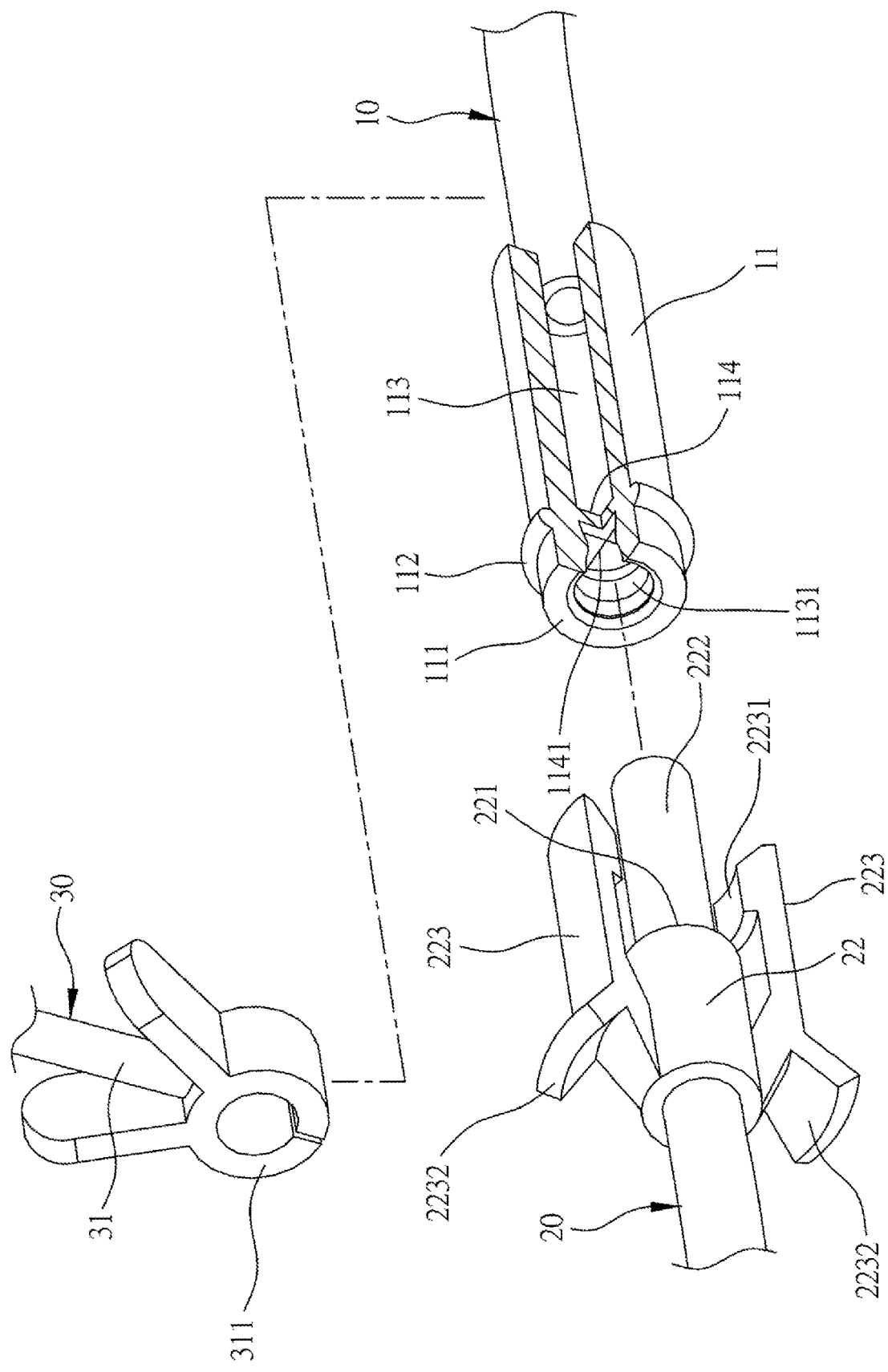
FIG. 2 is a partially exploded view of the present invention.
Figure 3:
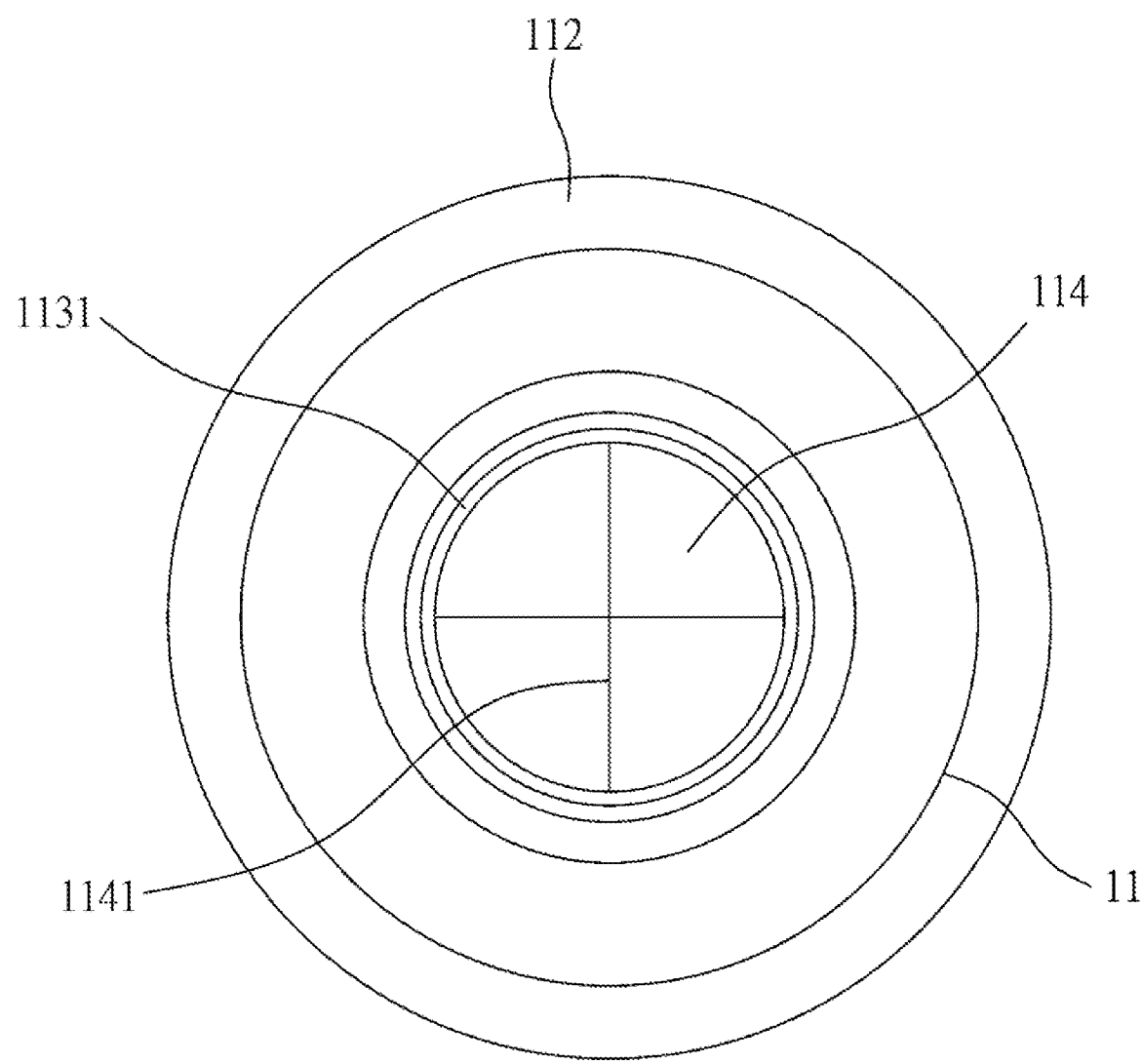
FIG. 3 is an end view of the first connector of the present invention.

Referring to FIG. 1 to FIG. 3, the present invention provides a food reflux reducing two-piece nasogastric tube, comprising a first tube body 10, a second tube body 20, and a fixing device 30.

The first tube body 10 comprises a first connector 11 disposed on one end thereof, and an insertion portion 12 disposed on another end thereof. A first positioning portion 111 is disposed on one end of the first connector 11 away from the first tube body 10. A ring-shaped protrusion edge 112 is disposed on an outer side of the first connector 11 in adjacent to the first positioning portion 111. The first connector 11 comprises a through hole 113 formed in an axial direction and connected with the first tube body 10. The through hole 113 comprises an elastic seal portion 114 disposed in adjacent to the first positioning portion 111, and the seal portion 114 is provided with a cross break 1141 which is normally in a sealing status. The inner edge of the through hole 113 comprises a ring-shaped convex portion 1131 disposed between the seal portion 114 and the first positioning portion 111.

The second tube body 20 comprises an irrigation portion 21 disposed on one end and a second connector 22 disposed on another end. A second positioning portion 221 is disposed on one end of the second connector 22 away from the second tube body 20, and an insertion combination tube 222 extends from the second positioning portion 221, wherein the insertion combination tube 222 is connected with the second tube body 20. The second connector 22 comprises two elastic arms 223 extending from an outer side of the second connector 22 toward the insertion combination tube 222, with a hook portion 2231 disposed on a distal end of each of the two elastic arms 223. Each of the two elastic arms 223 comprises a press portion 2232 which is disposed in adjacent to the second connector 22 and extending toward the second tube body 20, respectively. When the two press portions 2232 are pressed, the press portions 2232 drive the two elastic arms 223 to open.

The fixing device 30 comprises a fixing member 31, an adherence member 32, and a connection member 33. The fixing member 31 comprises a clamp ring 311 and a first rod body 312. The clamp ring 311 is disposed on one end of the first rod body 312. The clamp ring 311 detachably clamps the first tube body 10 in adjacent to or on the first connector 11 for providing a fixing effect. The connection member 33 comprises a second rod body 331 and a universal ball part 332. One end of the second rod body 331 is connected with the universal ball part 332, and another end of the second rod body 331 is pivotally and adjustably connected with the adherence member 32. Therein, the adherence member 32 is able to be adhered on the nose of the patient. The connection member 33 is pivotally and adjustably connected with one end of the first rod body 312 of the fixing member 31 through the universal ball part 332. The first rod body 312 of the fixing member 31 and the second rod body 331 of the connection member 33 are held up with the universal ball part 332 serving as the support, and the first rod body 312 and the second rod body 331 are prevented from contacting the nose, so as to improve the fixing effect of the first tube body 10 which is retained in the patient body.

Figure 4:
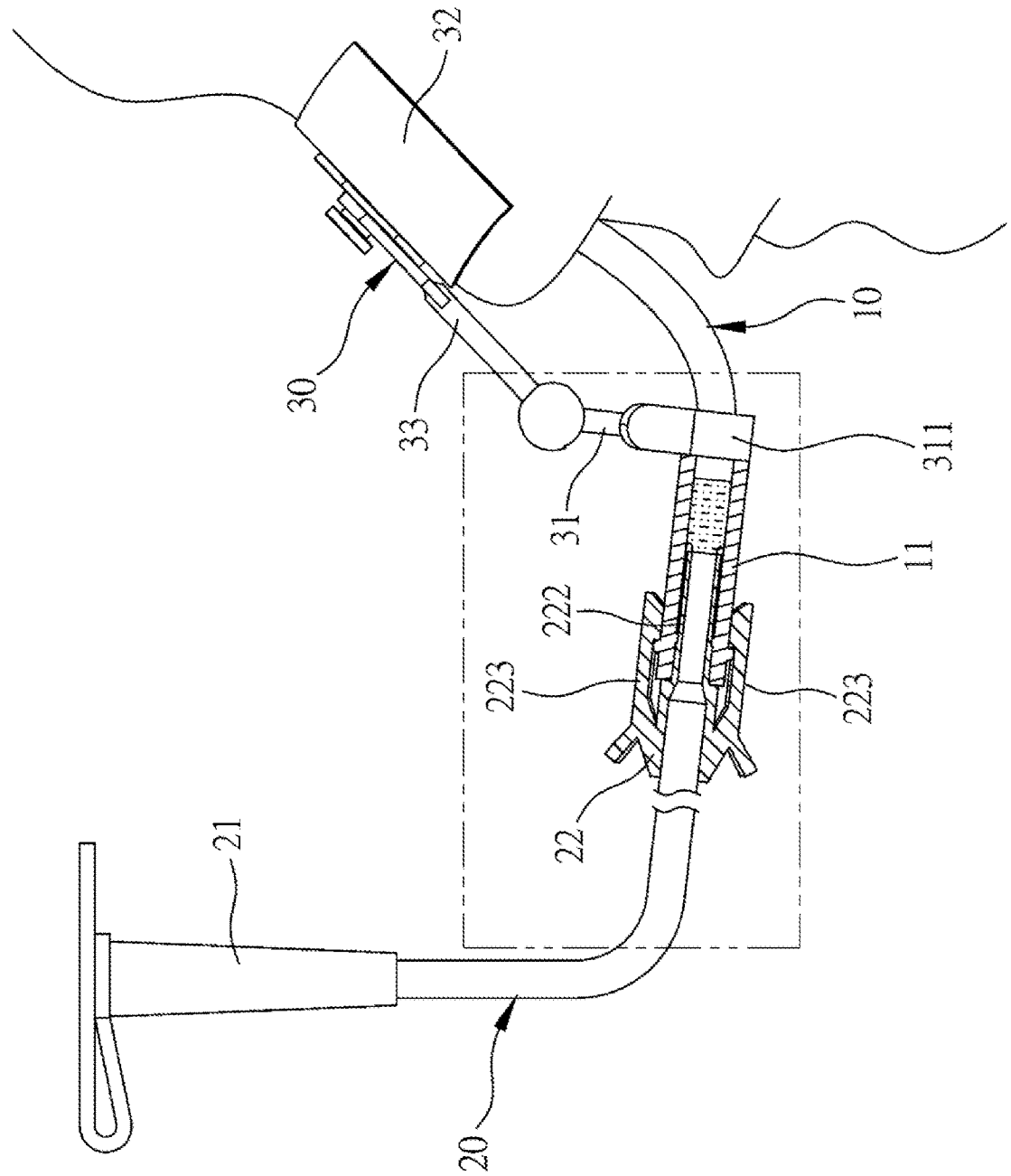
FIG. 4 is a schematic view illustrating the usage status of the present invention.
Figure 5:
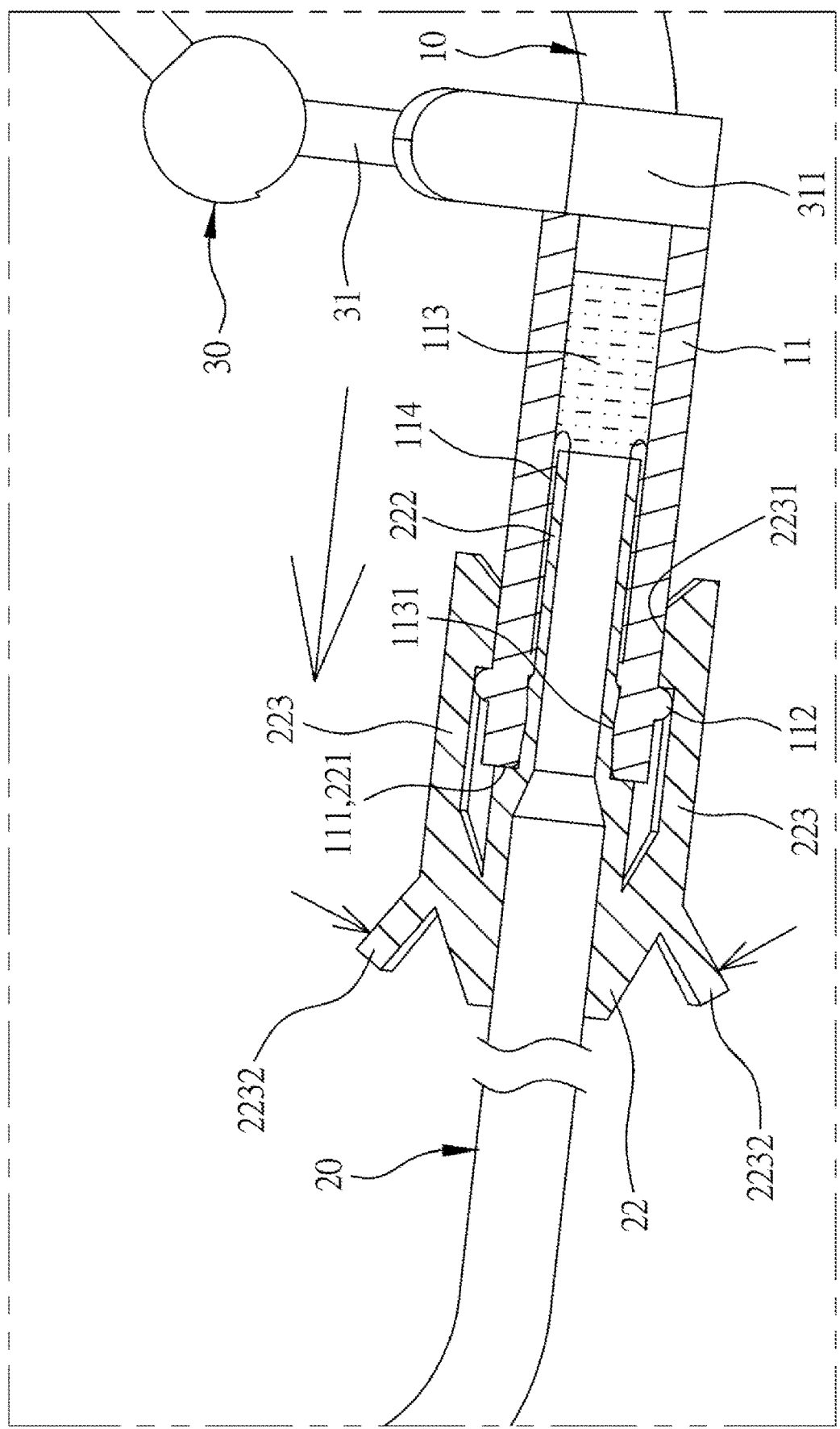
FIG. 5 is a first schematic view illustrating the operation status of the second tube body being disassembled from the first tube body.
Figure 6:
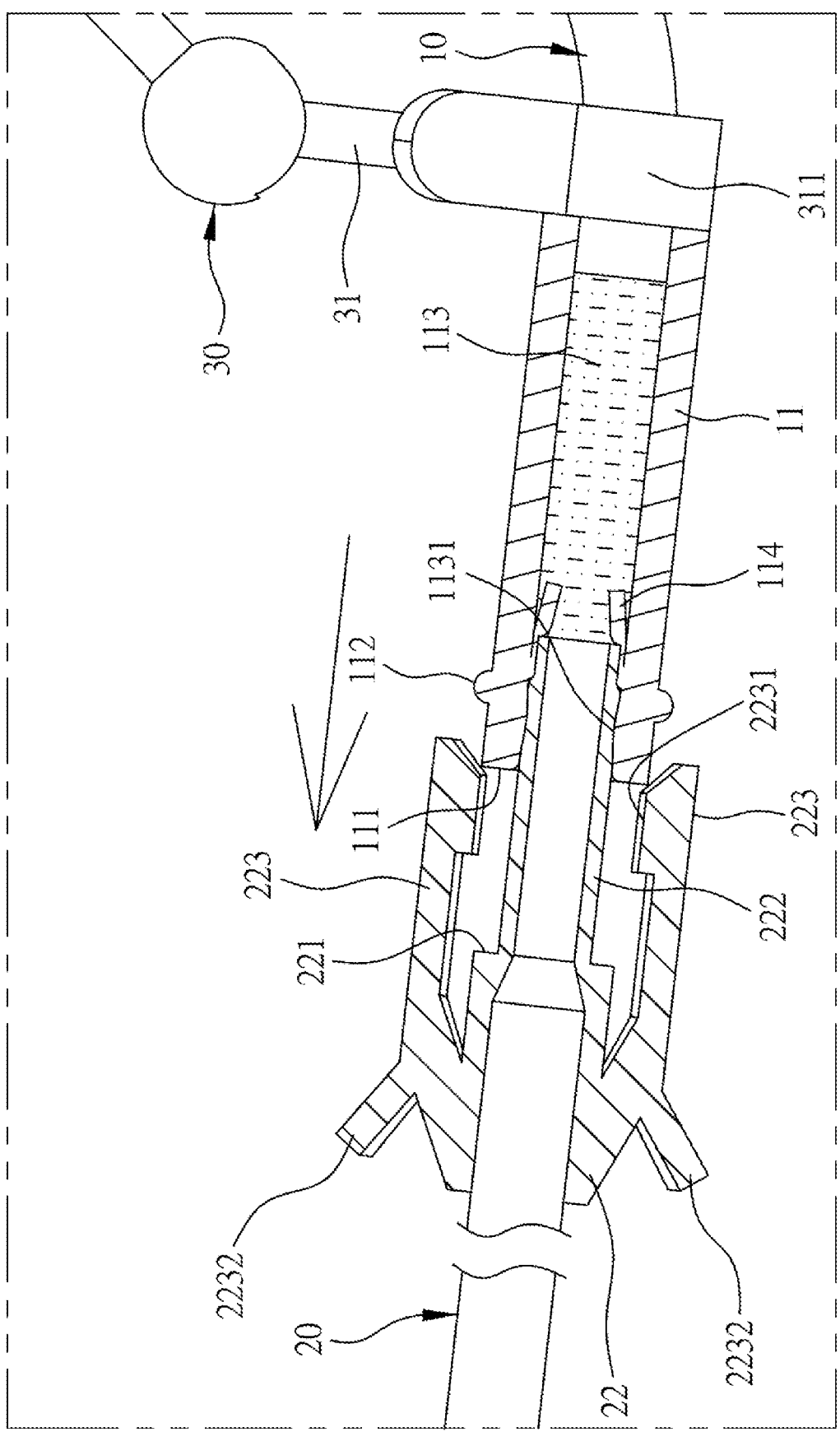
FIG. 6 is a second schematic view illustrating the operation status of the second tube body being disassembled from the first tube body.
Figure 7:
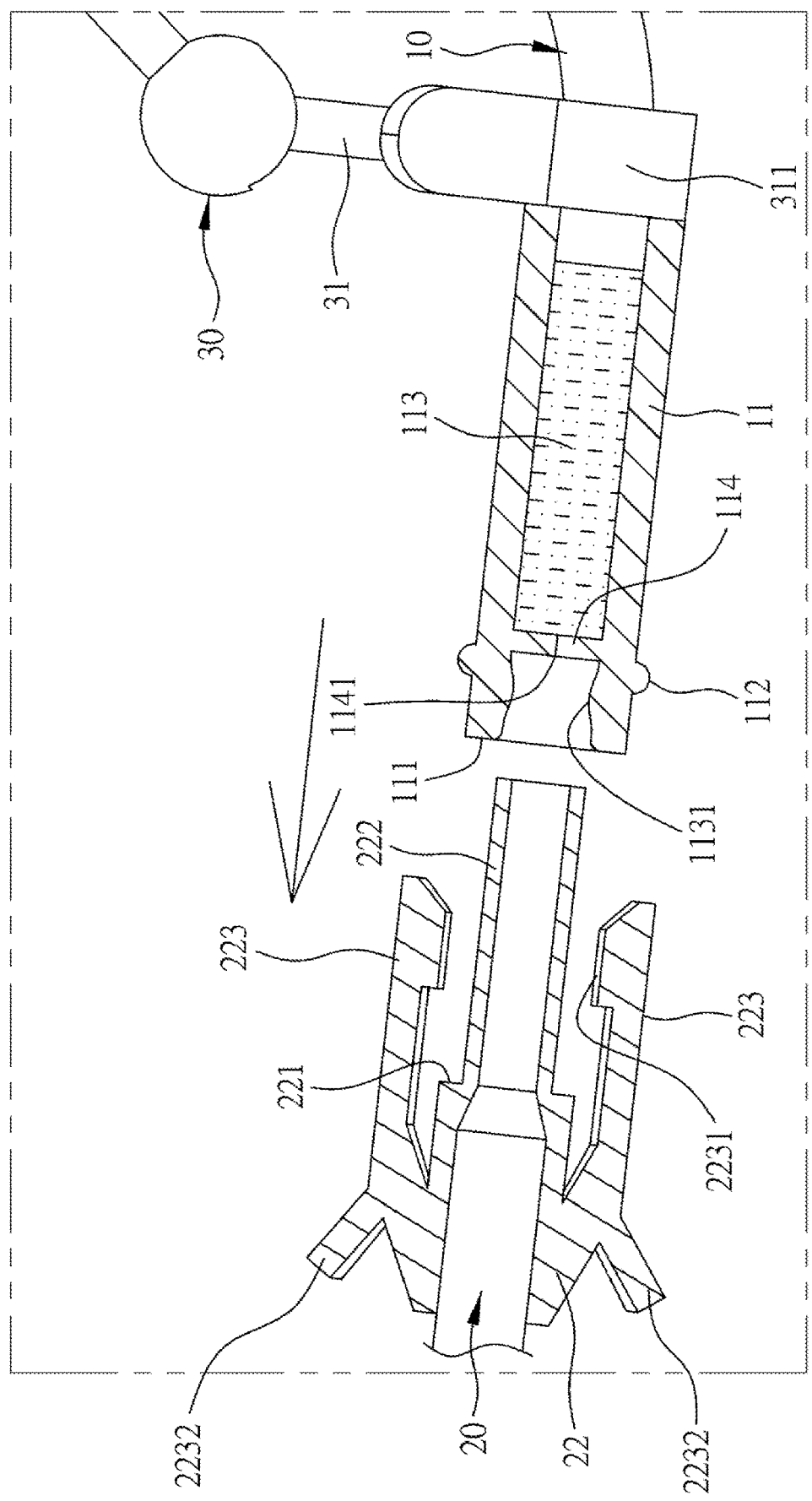
FIG. 7 is a third schematic view illustrating the operation status of the second tube body being disassembled from the first tube body.
Figure 8:
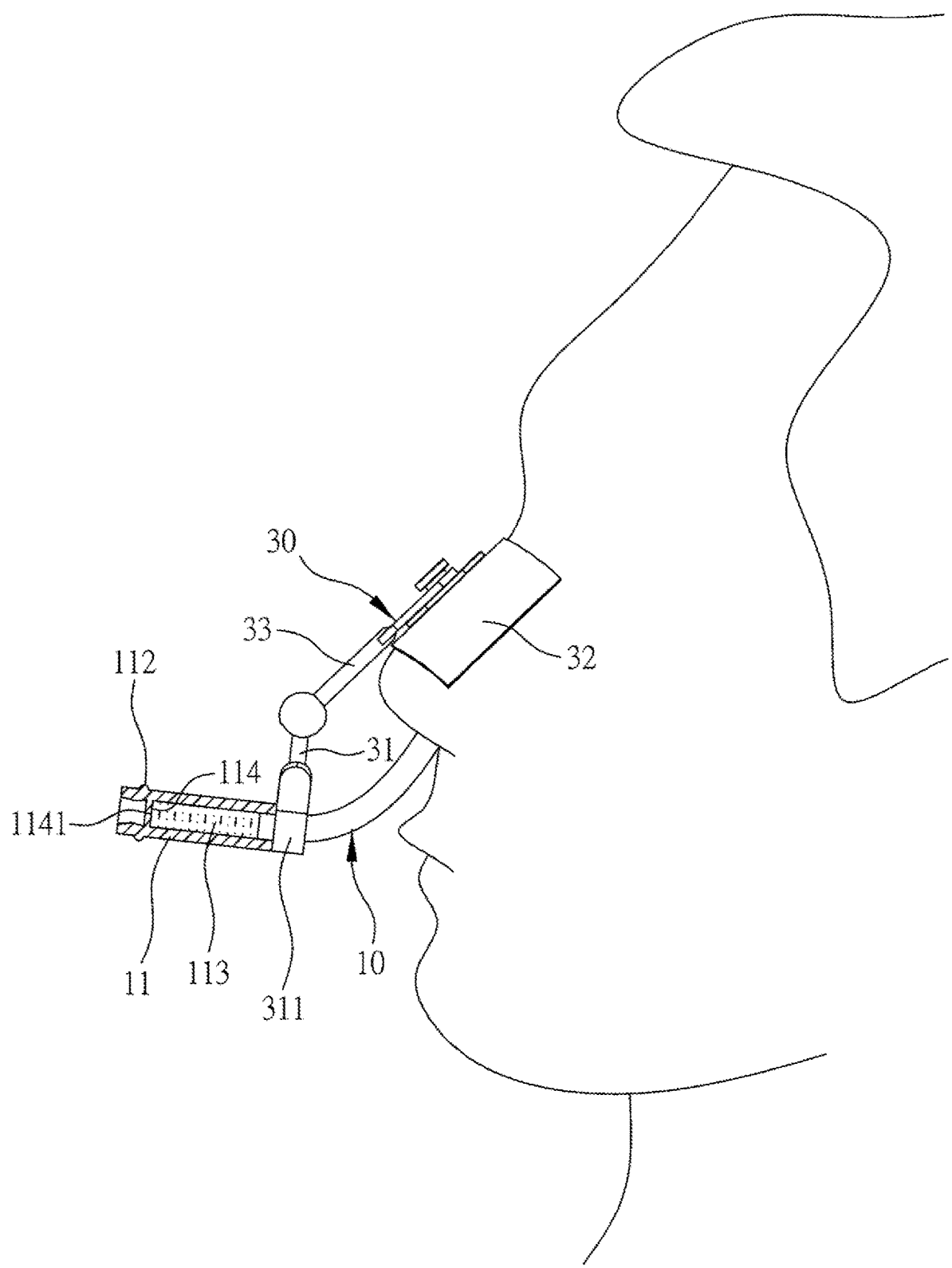
FIG. 8 is a schematic view illustrating the second tube body after being disassembled from the first tube body.

During the irrigation feeding operation, referring to FIG. 4, the second connector 22 is inserted into the through hole 113 of the first connector 11 through the insertion combination tube 222, such that the insertion combination tube 222 expands the cross break 1141, and the outer periphery of the insertion combination tube 222 tightly abuts against the convex portion 1131, thereby forming a sealing status. Also, with the second positioning portion 221 abutting against the first positioning portion 111, and the hook portion 2231 of the two elastic arms 223 hooking the protrusion edge 112, the second connector 22 is connected with the first connector 11, and the second tube body 20 is connected with the first tube body 10, such that insertion portion 12 of the first tube body 10 passes from the nasal cavity through the esophagus into the stomach of the patient, allowing a food fluid to be provided from a feeding syringe into the irrigation portion 21, and accordingly enter the stomach of the patient for supplying necessary nutrition.

When the irrigation feeding operation is complete, referring to FIG. 5 to FIG. 8, the two press portions 2232 are pressed to open the two elastic arms 223, such that the hook portion 2231 of the elastic arms 223 leaves the protrusion edge 112, and the second connector 22 of the second tube body 20 is disassembled from the first connector 11 of the first tube body 10. When the second connector 22 of the second tube body 20 is removed, the cross break 1141 of the first connector 11 is automatically restored to the sealing status by the elasticity of the seal portion 114, thereby preventing external matters from entering the first tube body 10 to cause infection, and also preventing the reflux of food residue in the first tube body 10. Also, with only the first tube body 10 being retained in the patient body, the aesthetic appearance and comfort of the patient after the installation of the nasogastric tube is improved, and the possibility of the nasogastric tube being accidentally pulled is significantly reduced.

With the foregoing configuration, the present invention achieves following advantages.

Regarding the food reflux reducing two-piece nasogastric tube of the present invention, when the insertion combination tube 222 of the second connector 22 is inserted into the through hole 113 of the first connector 11 for combination, the insertion combination tube 222 expands the cross break 1141, and the outer periphery of the insertion combination tube 222 tight abuts against the convex portion 1131; when the second tube body 20 is removed from the first tube body 10, the cross break 1141 of the first connector 11 is automatically sealed. Therefore, the present invention significantly increases the convenience of usage, and greatly reduces the discomfort of patient and the situation of food reflux. Also, the conditions of the cover falling or the user forgetting to put on the cover are avoided.

Although particular embodiments of the invention have been described in detail for purposes of illustration, various modifications and enhancements may be made without departing from the scope of the invention. Accordingly, the invention is not to be limited except as by the appended claims.

What is claimed is:

1. A food reflux reducing two-piece nasogastric tube, comprising:
   a first tube body having a first connector on one end and an insertion portion on another end, a first positioning portion disposed on one end of the first connector away from the first tube body, a protrusion edge being disposed on an outer side of the first connector adjacent to the first positioning portion, the first connector comprising a through hole formed in an axial direction and connected with the first tube body, the through hole comprising an elastic seal portion disposed adjacent to the first positioning portion, the seal portion being provided with a cross break which is normally in a sealing status, a convex portion being disposed on an inner edge of the through hole between the seal portion and the first positioning portion;
   a second tube body having an irrigation portion disposed on one end and a second connector disposed on another end, a second positioning portion being disposed on one end of the second connector away from the second tube body, an insertion combination tube extending from the second positioning portion, the insertion combination tube being connected with the second tube body, two elastic arms extending from an outer side of the second connector toward the insertion combination tube, with a hook portion disposed on a distal end of each of the two elastic arms; wherein, when in use, the insertion combination tube is inserted into the through hole of the first connector, such that the insertion combination tube expands the cross break, an outer periphery of the insertion combination tube tightly contacts and abuts against the convex portion, the second positioning portion abuts against the first positioning portion, and the hook portion of the two elastic arms hooks the protrusion edge, such that the second connector is connected with the first connector, and the second tube body is connected with the first tube body; and a fixing device comprising a fixing member, an adherence member, and a connection member, the fixing member comprising a clamp ring and a first rod body, the clamp ring disposed on one end of the first rod body, the clamp ring detachably clamping the first connector of the first tube body, the connection member comprising a second rod body and a universal ball part, one end of the second rod body being connected with the universal ball part, another end of the second rod body being pivotally and adjustably connected with the adherence member, the adherence member being configured to be adhered on a patient's nose, the connection member being pivotally and adjustably connected with one end of the first rod body of the fixing member through the universal ball part, the first rod body of the fixing member and the second rod body of the connection member being held up with the universal ball part serving as a support, such that the first rod body and the second rod body are configured to be prevented from contacting the patient's nose.

2. The food reflux reducing two-piece nasogastric tube of claim 1, wherein each of the two elastic arms comprises a press portion which is disposed adjacent to the second connector and extending toward the second tube body, respectively; when the two press portions are pressed, the press portions drive the two elastic arms to open.

3. The food reflux reducing two-piece nasogastric tube of claim 1, wherein the protrusion edge is formed in a ring shape.

4. The food reflux reducing two-piece nasogastric tube of claim 1, wherein the convex portion is formed in a ring shape.

* * * * *